US011213418B2

United States Patent
Knotts et al.

(10) Patent No.: US 11,213,418 B2
(45) Date of Patent: Jan. 4, 2022

(54) EXERCISE AND STRETCHING DEVICE

(71) Applicants: Joshua Braden Knotts, Tulsa, OK (US); Jessica Barrera Knotts, Tulsa, OK (US)

(72) Inventors: Joshua Braden Knotts, Tulsa, OK (US); Jessica Barrera Knotts, Tulsa, OK (US)

( * ) Notice: Subject to any disclaimer, the term of this patent is extended or adjusted under 35 U.S.C. 154(b) by 0 days.

(21) Appl. No.: 16/993,631

(22) Filed: Aug. 14, 2020

(65) Prior Publication Data

US 2021/0045908 A1    Feb. 18, 2021

Related U.S. Application Data

(60) Provisional application No. 62/886,650, filed on Aug. 14, 2019.

(51) Int. Cl.
*A61F 5/042* (2006.01)
*A61H 1/02* (2006.01)
(Continued)

(52) U.S. Cl.
CPC ........... *A61F 5/042* (2013.01); *A61H 1/0218* (2013.01); *A61H 1/0296* (2013.01); *A63B 21/02* (2013.01);
(Continued)

(58) Field of Classification Search
CPC ..... A63B 21/04; A63B 21/07; A63B 21/0414; A63B 21/0421; A63B 21/0425; A63B 21/0435; A63B 21/0442; A63B 21/045; A63B 21/0455; A63B 21/055; A63B 21/0552; A63B 21/0555; A63B 21/0557; A63B 2225/00; A63B 2225/09; A63B 2225/093; A63B 23/00; A63B 23/02; A63B 23/025; A63B 23/03; A63B 23/035; A63B 23/03508; A63B 23/03516; A63B 23/04; A63B 23/12; A63B 23/1209; A63B 23/1218; A63B 23/1227; A63B 23/1236; A63B 23/1245; A63B 23/1254; A63B 23/1263; A63B 23/1272; A63B 23/1281; A63B 23/129; A63B 23/14; A63B 23/16; A63B 2023/003; A63B 2023/006; A63B 2023/0411; A63B 22/00; A63B 22/0002; A63B 22/0007; A63B 22/0012;
(Continued)

(56) References Cited

U.S. PATENT DOCUMENTS 1,734,238 A * 11/1929 Sweeney ............ A63B 21/4009
  482/123
1,866,024 A *  7/1932 Gailey ............... A63B 21/0004
  482/125

(Continued)

*Primary Examiner* — Loan B Jimenez
*Assistant Examiner* — Thao N Do
(74) *Attorney, Agent, or Firm* — Boudwin Intellectual Property; Daniel Boudwin

(57) ABSTRACT

An exercise and stretching device is shown and described. The exercise and stretching device includes a connection cable located through a rigid tube. The rigid tube has a curvature. There are connectors at each end of the connection cable. The connectors are connected to resistance bars. The resistance bars have an aperture located at each end of the bar, wherein an aperture of each bar accepts the connectors. A handle is connected to the aperture opposite the connector.

6 Claims, 6 Drawing Sheets

(51) Int. Cl.
*A63B 21/02* (2006.01)
*A63B 21/055* (2006.01)
*A63B 21/04* (2006.01)

(52) U.S. Cl.
CPC ...... *A63B 21/0442* (2013.01); *A63B 21/0552* (2013.01); *A63B 21/0557* (2013.01); *A61H 2201/0192* (2013.01); *A61H 2201/1609* (2013.01); *A61H 2201/1635* (2013.01)

(58) Field of Classification Search
CPC ............ A63B 22/0015; A63B 22/0017; A63B 22/0023; A63B 22/02; A63B 22/0207; A63B 22/0228; A63B 2022/0033; A63B 2022/0035; A63B 2005/163; A63B 51/023; A61H 2003/006; A61H 2201/0153; A61H 1/02; A61H 1/0218; A61H 1/0296; A61H 3/008; A61F 5/042
USPC .................. 482/124, 131, 126, 91
See application file for complete search history.

(56) References Cited

U.S. PATENT DOCUMENTS

| | | | | |
|---|---|---|---|---|
| 2,467,943 A * | 4/1949 | Mikell | ............... | A63B 21/0004 482/79 |
| 3,221,735 A * | 12/1965 | Goodman | ................ | A61H 1/00 602/33 |
| 4,969,643 A * | 11/1990 | Kroeker | ............. | A63B 21/0083 188/312 |
| 5,158,510 A * | 10/1992 | Lemire | .............. | A63B 21/4001 482/51 |
| 5,207,627 A | 5/1993 | Doran | | |
| 5,514,059 A | 5/1996 | Romney | | |
| 5,518,481 A * | 5/1996 | Darkwah | ........... | A63B 21/0004 482/126 |
| 5,885,196 A * | 3/1999 | Gvoich | .............. | A63B 21/0552 482/125 |
| 6,450,926 B1 * | 9/2002 | McKernan | ........ | A63B 21/0004 482/148 |
| 6,517,469 B1 * | 2/2003 | Mercier | ........... | A63B 21/00043 482/121 |
| 8,343,018 B2 | 1/2013 | Moulton | | |
| 9,333,385 B2 * | 5/2016 | Hinds | .................... | A63B 21/02 |
| 9,849,325 B1 | 12/2017 | Robinson | | |
| 9,914,012 B2 * | 3/2018 | Walter | ............... | A63B 21/4039 |
| 2005/0054497 A1 * | 3/2005 | Hull | .................. | A63B 21/0552 482/110 |
| 2005/0113222 A1 * | 5/2005 | Dovner | ............. | A63B 21/0004 482/121 |
| 2008/0269030 A1 * | 10/2008 | Hoffman | .............. | A61H 1/0218 482/142 |
| 2009/0082183 A1 * | 3/2009 | Haynes | ............. | A63B 21/4025 482/124 |
| 2010/0204014 A1 * | 8/2010 | Hoffman | ............. | A63B 21/055 482/8 |
| 2010/0285939 A1 * | 11/2010 | Latronica | ............... | A63B 21/16 482/139 |
| 2011/0130253 A1 * | 6/2011 | Fuller | .................. | A63B 21/169 482/122 |
| 2011/0230314 A1 * | 9/2011 | Hoffman | ............ | A63B 24/0062 482/51 |
| 2011/0237410 A1 * | 9/2011 | Perez | ................. | A63B 21/0557 482/129 |
| 2011/0275493 A1 * | 11/2011 | Perez | ................... | A61H 1/0292 482/91 |
| 2011/0312477 A1 * | 12/2011 | Wiseman | ........... | A63B 21/0552 482/126 |
| 2012/0040808 A1 * | 2/2012 | Khademi | ............. | A61H 1/0285 482/124 |
| 2012/0329618 A1 * | 12/2012 | White | ................ | A63B 21/1636 482/126 |
| 2012/0329620 A1 * | 12/2012 | White | ..................... | A63B 7/02 482/131 |
| 2013/0053225 A1 * | 2/2013 | Meyer | ................ | A63B 21/4043 482/124 |
| 2013/0203567 A1 * | 8/2013 | Thomas | ............. | A63B 21/4025 482/124 |
| 2014/0073496 A1 * | 3/2014 | Bannerman | ........ | A63B 23/0355 482/139 |
| 2014/0274593 A1 * | 9/2014 | Kelly | ................. | A63B 21/4043 482/105 |
| 2014/0342884 A1 * | 11/2014 | Aldridge | ............ | A61H 1/0237 482/131 |
| 2015/0290020 A1 | 10/2015 | Carpenter | | |
| 2018/0178050 A1 * | 6/2018 | Prihar | ................ | A63B 21/4035 |
| 2019/0240529 A1 * | 8/2019 | Burkinshaw | ....... | A63B 21/4043 |
| 2021/0086015 A1 * | 3/2021 | Sun | ...................... | A63B 21/028 |

* cited by examiner

EXERCISE AND STRETCHING DEVICE

CROSS REFERENCE TO RELATED APPLICATIONS

This application claims the benefit of U.S. Provisional Application No. 62/886,650 filed on Aug. 14, 2019. The above identified patent application is herein incorporated by reference in its entirety to provide continuity of disclosure.

BACKGROUND OF THE INVENTION

The present invention relates to exercise and stretching devices. More particularly, the exercise and stretching device is a device that provides joint decompression, increased range of motion, and improves mobility in the body. This device affords a self-administered relief of joint pain, improved mobility, and an enhanced quality of life in the comfort of their home.

Pain and stiffness limit function and range of motion in a joint. Potentially leading to degenerative orthopedic conditions and limitations to quality of life. Many individuals experience joint pain, stiffness near the neck, back, hip, shoulder and elsewhere. Many individuals lack functional innervation.

Pain and stiffness limit function and range of motion in a joint and that loss is a problem that leads to degenerative conditions, which is why the utilization of this device is which is beneficial to the user.

Consequently, there is a need for an improvement in the art of stretching and loosening the muscles of the body. The present invention substantially diverges in design elements from the known art while at the same time solves a problem many people face when having tight muscles. Since the device is self-administered, the user performs stretches with the device at home and has been clinically shown to improve mobility, improved range of motion, and decrease pain. In this regard the present invention substantially fulfills these needs.

SUMMARY OF THE INVENTION

The present invention provides an exercise and stretching device wherein the same can be utilized for providing convenience for the user when stretching one's body to help avoid discomfort and injury. The exercise and stretching device is comprised of a connection cable located through a rigid tube. The rigid tube has a curvature. There are connectors at each end of the connection cable. The connectors are connected to resistance bars. The resistance bars have an aperture located at each end of the bar, wherein an aperture of each bar accepts the connectors. A handle is connected to the aperture opposite the connector.

Another object of the exercise and stretching device is to have the handle be a rope handle.

Another object of the exercise and stretching device is to have a bearing within each aperture of the apertures of the resistance bars.

Another object of the exercise and stretching device is to have the resistance bars be metal resistance bars.

Another object of the exercise and stretching device is to have the rigid tube have a padded tube placed therearound.

Another object of the exercise and stretching device is to have a second padded tube placed around the first padded tube.

Another object of the exercise and stretching device is to have an adjustable strap attached to each of the handles.

Another object of the exercise and stretching device is to have the connectors be carabiners.

Another object of the exercise and stretching device is to have the curved tube conform to an average human neck.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
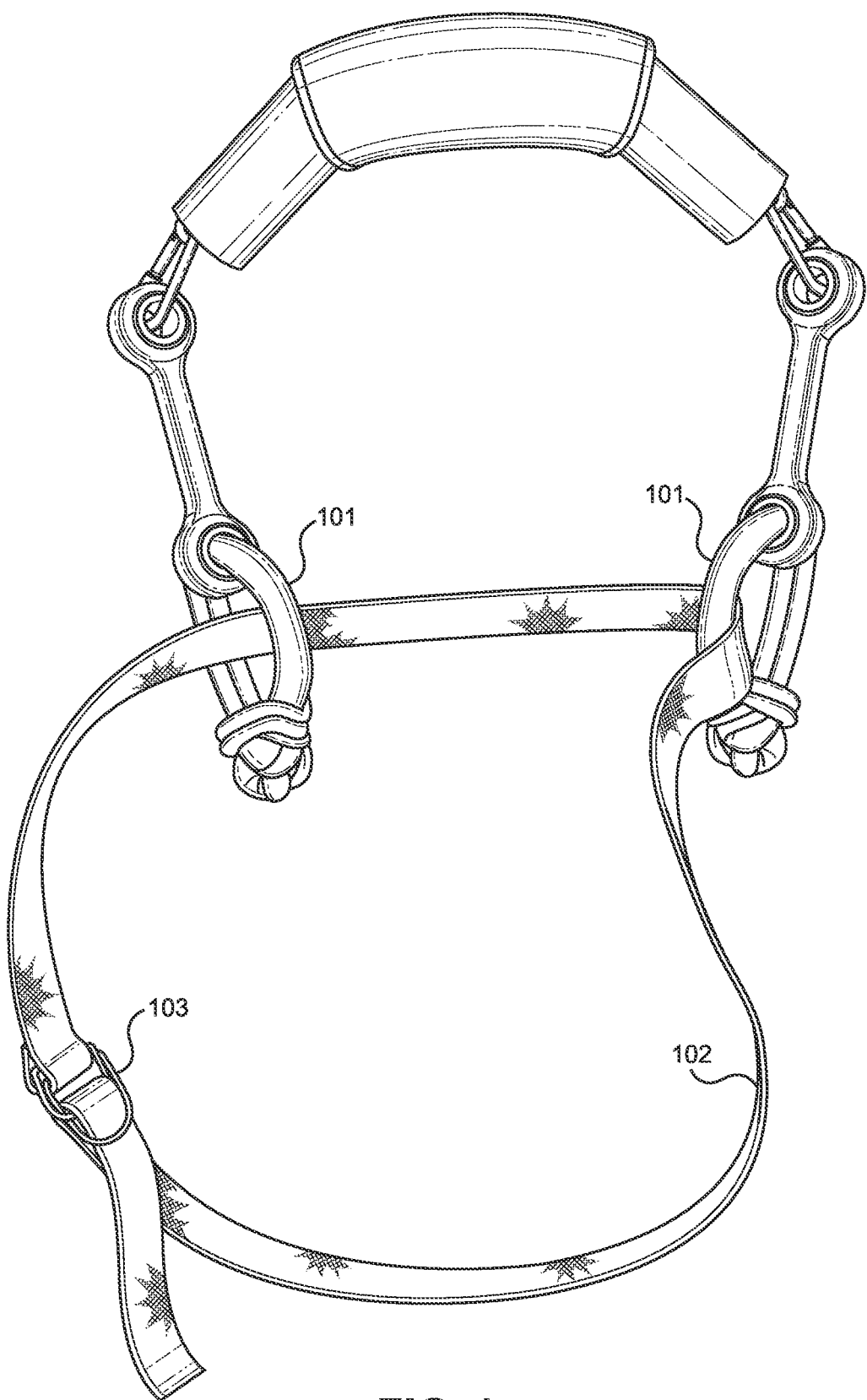
FIG. 1 shows a perspective view of an embodiment of the exercise and stretching device.

Reference is made herein to the attached drawings. Like reference numerals are used throughout the drawings to depict like or similar elements of the exercise and stretching device. For the purposes of presenting a brief and clear description of the present invention, a preferred embodiment will be discussed as used for the exercise and stretching device. The figures are intended for representative purposes only and should not be considered to be limiting in any respect.

Referring now to FIG. 1, there is shown a perspective view of an embodiment of the exercise and stretching device. The exercise and stretching device is designed to allow individuals to stretch all manner of body aliments thus relieving pain. The exercise and stretching device is comprised of at least a pair of handles 101 and a connection cable. The connection cable will be detailed in the description of FIG. 4. In the shown embodiment, the pair of handles 101 are rope handles. Specifically, the pair of handles 101 are lengths of rope tied together, forming loops. This will allow for the handles 101 to be easily held. In some embodiments, this will further allow for additional elements to be added to the exercise and stretching device as described herein.

In other embodiments, the pair of handles 101 are lengths of rope not tied together. This will allow the pair of handles 101 to be straight handles. In one embodiment, each pair of handles 101 has a knot on the end which will ensure the user's hand does not slip from the handle.

In one embodiment there, is a strap 102 connected to the pair of handles 101. In one embodiment, the strap 102 is an exercise resistance band. In another embodiment, the strap 102 is an inelastic woven strap. In one embodiment, the strap 102 is connected together forming a loop. In this way, the strap 102 can be looped around body parts in order to allow for stretching. In one embodiment, the strap 102 has a buckle 103 holding the strap 102 together forming the loop. In a further embodiment, the buckle 103 is also an adjuster. The adjuster will allow the strap's 102 length to be adjusted and, therefore, adjust the size of the loop.

Figure 2:
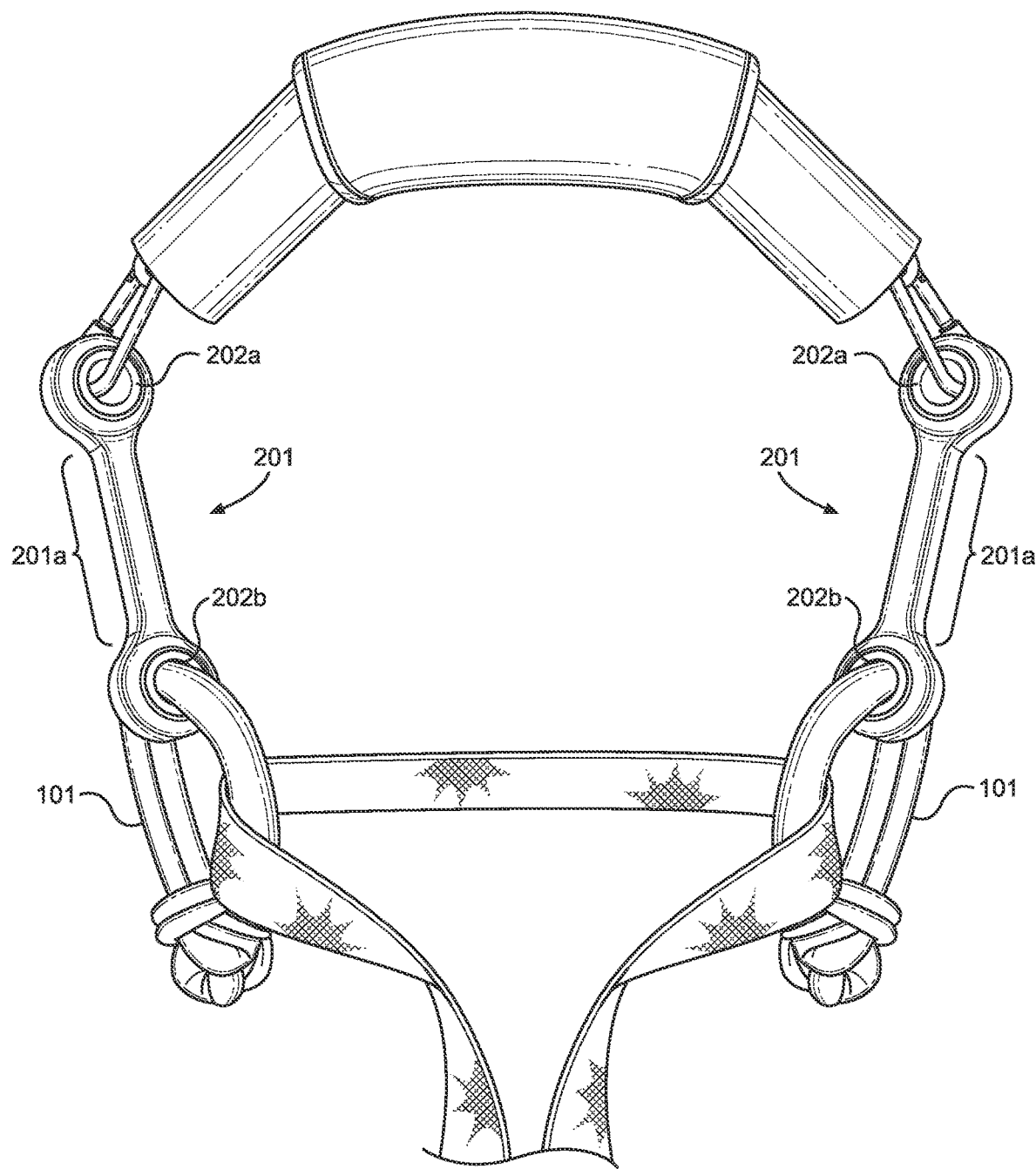
FIG. 2 shows a close-up top down view of an embodiment of the exercise and stretching device.

Referring now to FIG. 2, there is shown a close up top down view of an embodiment of the exercise and stretching device. In one embodiment, there are resistance bars 201 attached to the connection cable. The resistance bars 201 are then connected to the pair of handles 101. In one embodiment, the resistance bars 201 are made from metal. In another embodiment, the resistance bars 201 are made from other suitable materials.

In some embodiments, resistance bars 201 have an aperture 202a, 202b at each end. In one embodiment, the first aperture 202a is connected directly to the connection cable. In another embodiment, there is a connector connecting the resistance bar 201 to the connection cable, as described in FIG. 3. The second aperture 202b of the resistance bar 201 is connected to one of the handles of the pair of handles 101.

In one embodiment, the resistance bars 201 have an ergonomic shape. In this embodiment, the resistance bars 201 will have a narrower width in a middle section 201a than that of the width at each end. In one embodiment, the resistance bars 201 will have a circular area at each end to contain the apertures 202a, 202b and a rectangular middle section 201a connecting the circular ends. This will allow the resistance bar 201 to be easily grasped.

Figure 3:
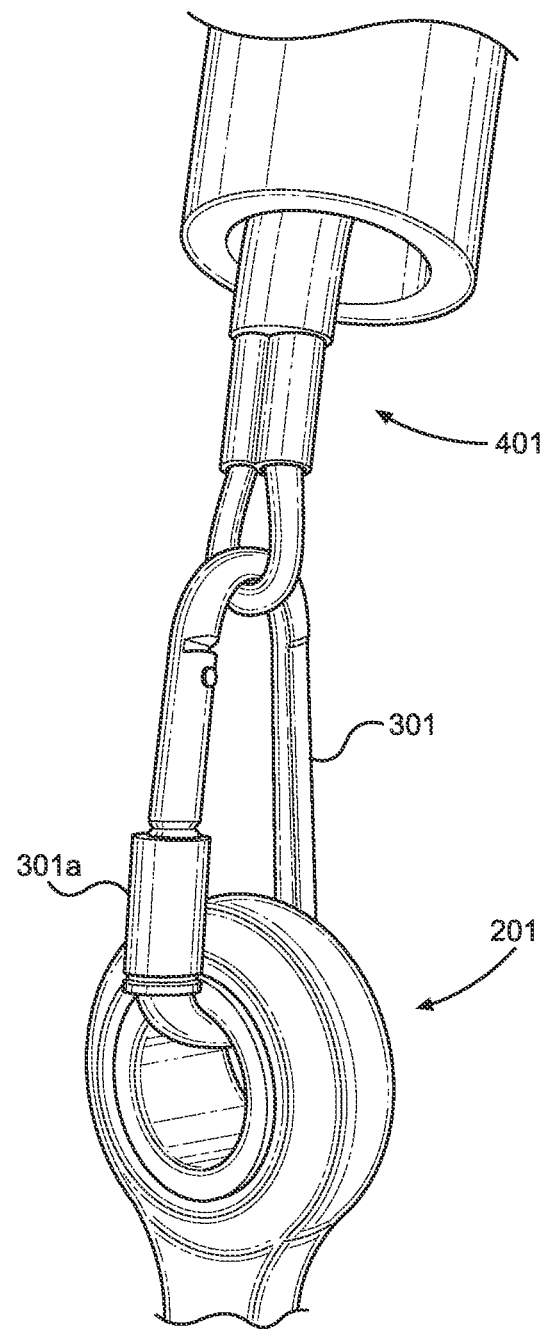
FIG. 3 shows a close-up view of an embodiment of connectors of the exercise and stretching device.

Referring now to FIG. 3, there is shown a close-up view of an embodiment of connections of the exercise and stretching device. In some embodiments, the exercise and stretching device includes a connector 301 which will connect the connection cable 401 to the resistance bars 201. In the shown embodiment the connector 301 is a carabiner. In some embodiments, the carabiner has a retention sheath 301a which can be positioned over the opening of the carabiner. This will hold the carabiner closed during use. In an alternate embodiment, the connector 301 is a chain link connector. In another embodiment, the connector 301 is an S-hook connector. In other embodiments, different types of connectors are used. These connectors generally allow free movement of the connection cable 401 and the resistance bars 201.

Figure 4:
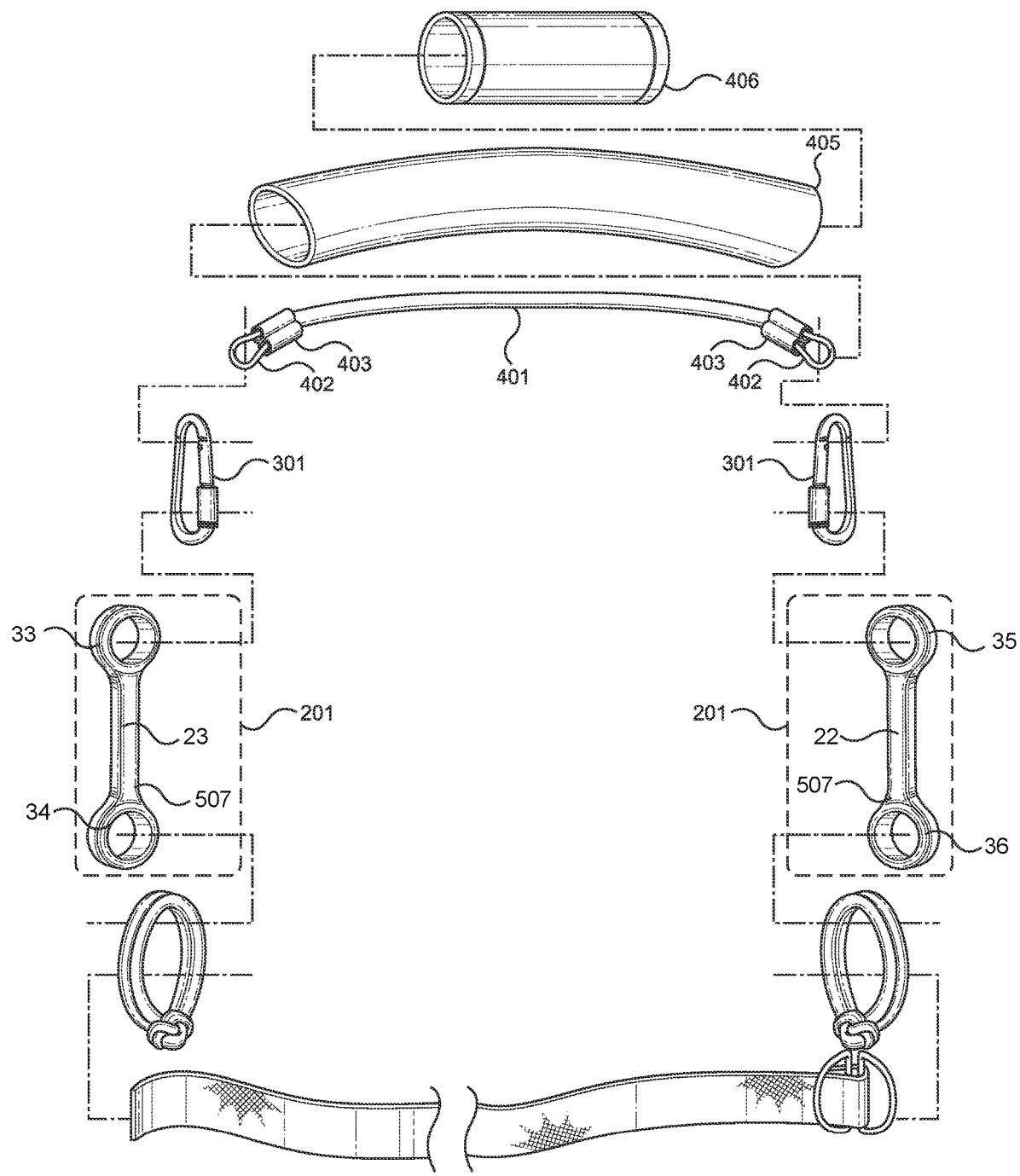
FIG. 4 shows an exploded view of an embodiment of the exercise and stretching device.

Referring now to FIG. 4, there is shown an exploded view of an embodiment of the exercise and stretching device. The exercise and stretching device includes a connection cable 401. In one embodiment, the connection cable 401 is a metal cable. In another embodiment, the connection cable 401 is a braided wire cable. In one embodiment, the connection cable 401 is a sheathed cable. This will prevent sweat or other corrosive elements from degrading the connection cable 401 over time.

In some embodiments, the connection cable 401 has loops 402 at both ends. The loops 402 will allow the connection cable 401 to be connected to the connectors 301 or directly to the resistance bars 201. In one embodiment, the loops 402 are formed by cable clamps 403. In other embodiments, the loops 402 are created by braiding the connection cable 401 into itself.

The exercise and stretching device further includes at least a first sleeve 405. In one embodiment, the first sleeve 405 is a padded sleeve. In another embodiment, the first sleeve 405 is a hard, rigid sleeve. In one embodiment, there first sleeve 405 has a hard, rigid interior layer and a padded exterior layer. In one of the embodiments where the first sleeve 405 is a hard, rigid sleeve, the first sleeve 405 has a curvature to it. In one embodiment, the curvature of the first sleeve 405 is such that it will conform to an average adult human neck. This will provide comfort to the user. In other embodiments, the curvature is a gentle curve that will provide comfort when the first sleeve 405 is in contact with various rounded body parts.

In some embodiments, there is a second sleeve 406. The second sleeve 406 is configured to fit over at least a portion of the first sleeve 405. In one embodiment, the second sleeve 406 is an additional padded sleeve. This will provide additional comfort to the user. In another embodiment, the second sleeve 406 is made of a moisture wicking material. This will remove sweat from a user and wick it away for comfort.

Figure 5:
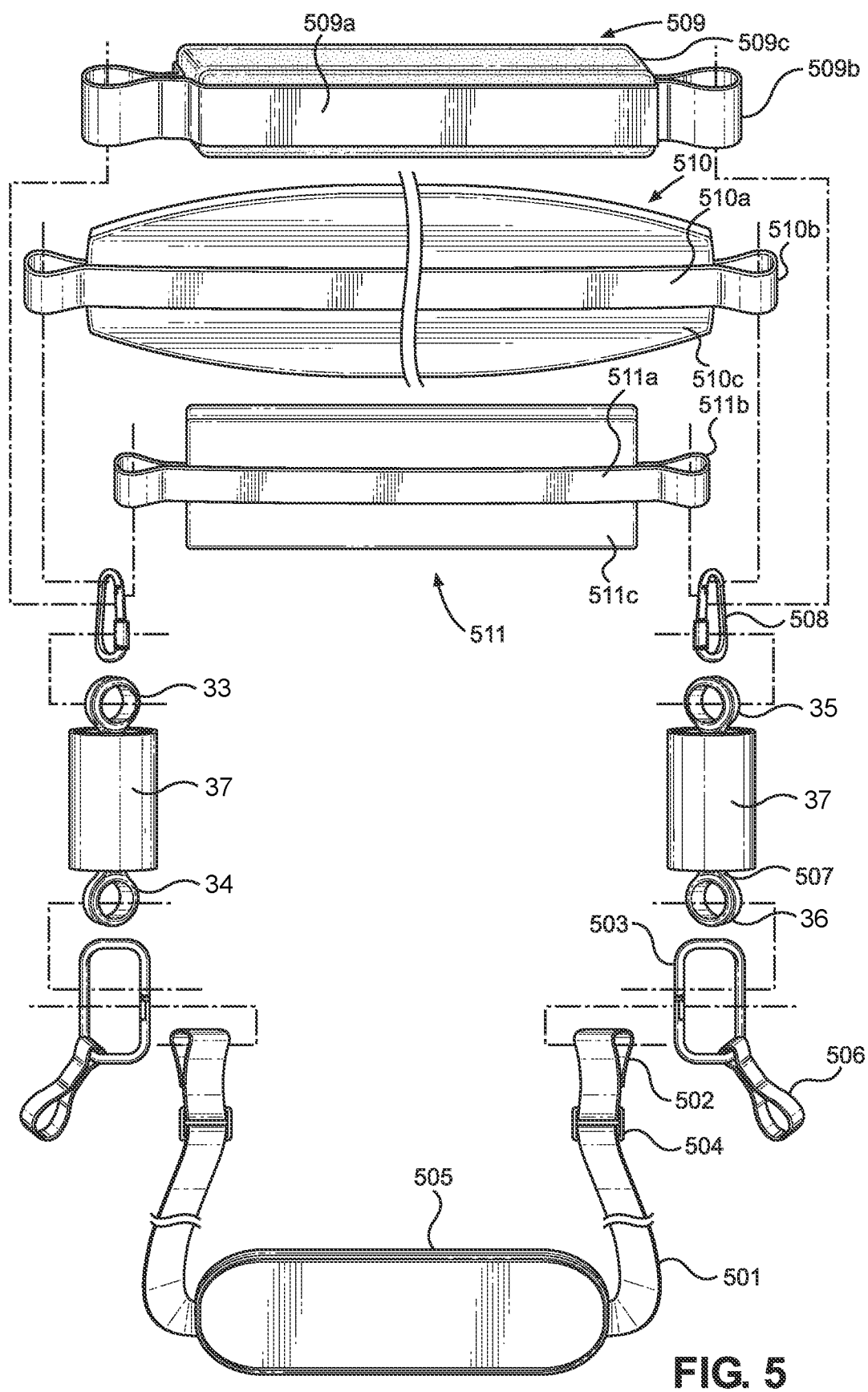
FIG. 5 shows an exploded view of an alternative embodiment of the exercise and stretching device.

Referring now to FIG. 5, there is shown an exploded view of an alternative embodiment of the exercise and stretching device. This embodiment of the exercise and stretching device includes a first strap 501. The first strap 501 has loops 502 located at each end. The loops 502 will secure to first connectors 503. In one embodiment, the first strap 501 is adjustable. In one embodiment, the first strap 501 has an adjuster 504 located at each end secured to the loops 502. In one embodiment, the first strap 501 has a padded section 505. In the shown embodiment, the padded section 505 is located in the middle the first strap 501. In one embodiment the padded section 505 is movable along the length of the first strap.

In one embodiment, the first connectors 503 are carabiners. In another embodiment, different connectors are used. In one embodiment, the first connectors 503 are further connected to handles 506. In one embodiment, the handles 506 are made from straps. In another embodiment, the handles 506 have a solid grasping portion. In one embodiment the solid grasping portion is a plastic tubing. This will prevent one's hands from being crushed in the handles 506. In the embodiment shown in FIG. 5, each handle 506 is secured to the connector 503 such that the handle 506 is positioned between the lower ring 34, 36 of the resistance bar 507 and the loop 502 of the strap or band 501.

The first connectors 503 are connected to resistance bars 507. In one embodiment, the resistance bars 507 are made from rubber and are therefore resilient. When the resistance bars 507 are stretched they will apply different amounts of resistance to the device. The resistance bars 507 have second connectors 508 located at the opposite end of the first connectors 503. In one embodiment, the second connectors 508 are carabiners. The connectors 507, 508 allow the resistance bar to be removable and replaceable, thus allowing a user to adjust overall resistance. In the embodiment shown in FIG. 5, a pair of resistance bars 507 are utilized. As shown in FIGS. 4 and 5, each resistance bar 507 is structured to include a central portion 22, 23 between the upper ring 33, 35 and the lower ring 34, 36 that is narrower than both the upper rings 33, 35 and lower rings 34, 36. Further, as shown in FIG. 5, each of the resistance bars 507 includes a cover 37 that encircles the resistance bar 507, which is cylindrical in the shown embodiment.

The second connectors 508 will connect to a support device 509, 510, 511. Each support device 509, 510, and 511 are meant to be used individually and not together. In different embodiments, different support devices may be used. Each different support device 509, 510, 511 will have a purpose for which it is suited. In one embodiment, the support device 509 is comprised of a strap 509a. The strap 509a will have loops 509b at each end. The strap 509a is secured to padded section 509c. In the shown embodiment, the padded section 509c is rectangular, however, in alternate embodiments, other shapes may be used.

In another embodiment, the support device 510 is comprised of a strap 510a. The strap 510a will have loops 510b at each end. The strap 510a is secured to a support section 510c. The support section 510c is tapers from thinner at the loops 510b to wider in the middle of the support section 510c. In this way the support device 510 is suited to fit along one's lower back.

A further support device 511 is comprised of a strap 511a. The strap 511a has loops 511b located at both ends. The strap 511a is secured to a support brace 511c. The support brace 511c is rectangular. This allows the support brace 511c to be used for a multitude of different items.

Figure 6:
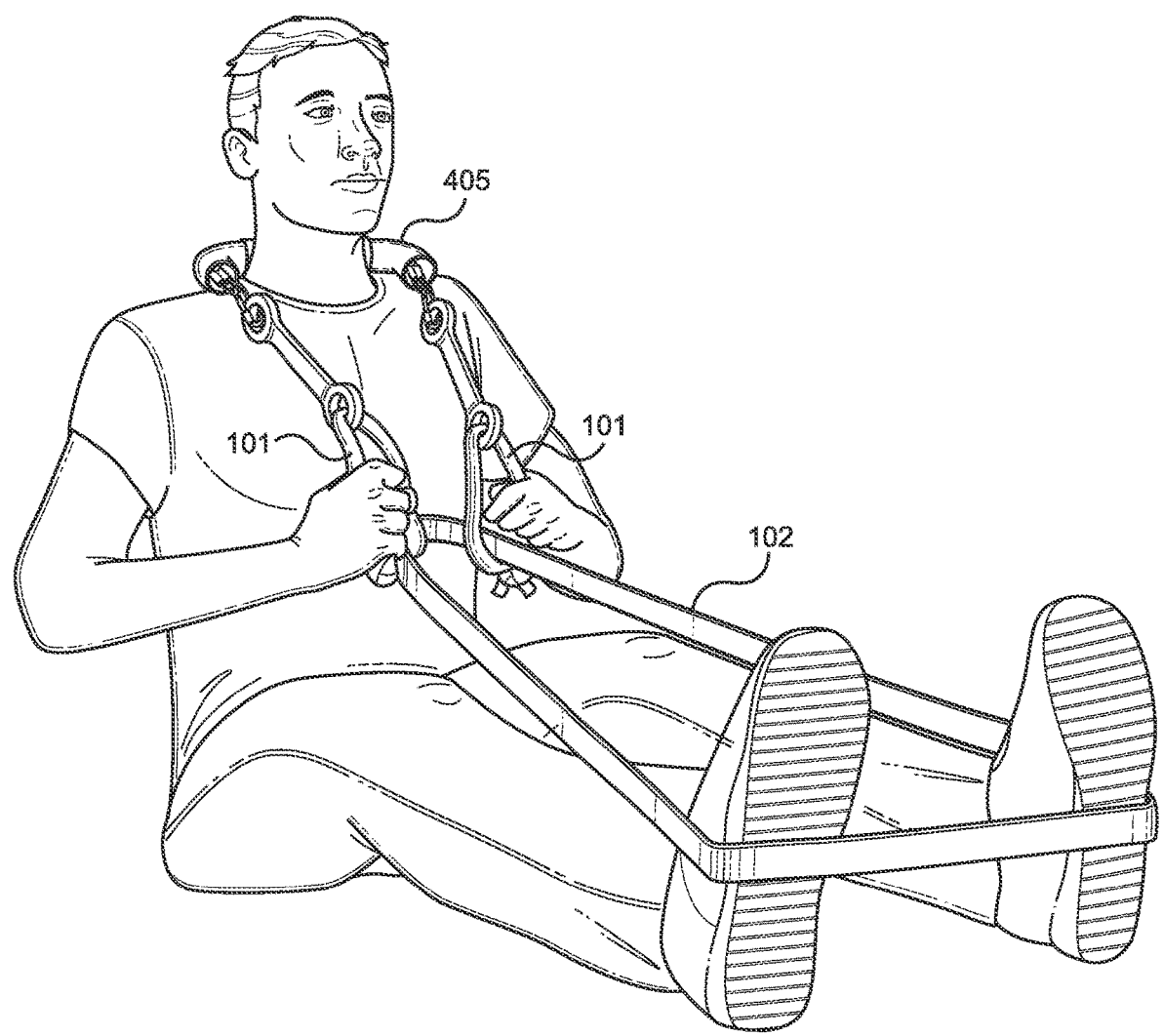
FIG. 6 shows an in-use view of an embodiment of the exercise and stretching device.

Referring now to FIG. 6, there is shown an in-use view of an embodiment of the exercise and stretching device. In use, the user places at least the first sleeve 405 about a body appendage, joint or other body part in direct effect of the muscle crossing that joint. The user will then grasp the pair of handles 101 and/or the strap 102. The user will then apply force via the hands or other appendage against the exercise and stretching device via at least the first sleeve 405. The joint, muscle, or other body part is stretched and/or activated against resistance, also known as agonist contract-relax (ACR). This activation will cause hypertrophy and relaxation of the engaged proximal muscles affected.

In another use a user may use the exercise and stretching device about the rear portion of the user's spine. The user may apply a pressure thereto, using the rear portion of the spine as a fulcrum wherein the user may stretch the arms outward creating decompression for joint impingement and/or joint distraction of the affected joints. In the shown embodiment, the strap 102 about the user's feet. In other embodiments, the strap 102 may be anchored to a fixed structure such as a door, or other body part for additional tension applied thereto used as a lever. The exercise and stretching device enables joint pain relief and enhanced mobility through decompression for joint impingement, joint distraction for joint compression, and increased range of motion for enhanced mobility to a desired area of the user's body.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An exercise and stretching device, comprising:
   a first band having a first loop disposed on a first end and a second loop disposed on a second end;
   a first connector removably secured to the first loop and a second connector removably secured to the second loop;
   a first resilient resistance bar having a first lower ring removably secured to the first connector;
   a first cover encircling the first resilient resistance bar;
   a second resilient resistance bar having a second lower ring removably secured to the second connector;
   a second cover encircling the second resilient resistance bar;
   a third connector removably secured to a first upper ring of the first resilient resistance bar, and a fourth connector removably secured to a second upper ring of the second resilient resistance bar; and
   a support device comprising a strap having a first end removably secured to the third connector and a second end removably secured to the fourth connector;
   wherein the first resilient resistance bar includes a first central portion between the first upper ring and the first lower ring that is narrower than the first upper ring and the first lower ring;
   wherein the second resilient resistance bar includes a second central portion between the second upper ring and the second lower ring that is narrower than the second upper ring and the second lower ring;
   wherein the first resilient resistance bar and the second resilient resistance bar are removable and replaceable to allow a user to adjust overall resistance.

2. The exercise and stretching device of claim 1, wherein the first band has an adjustable length.

3. The exercise and stretching device of claim 1, wherein the support device comprises padding.

4. The exercise and stretching device of claim 1, wherein the support device is tapered such that the support device includes a middle portion having a width greater than a width of a pair of opposing end portions.

5. The exercise and stretching device of claim 1, wherein the first cover and the second cover are cylindrical.

6. The exercise and stretching device of claim 1, further comprising a first handle secured to the first connector such that the first handle is positioned between the first lower ring of the first resilient resistance bar and the first loop of the first band, and a second handle secured to the second connector such that the second handle is positioned between the second lower ring of the second resilient resistance bar and the second loop of the first band.

* * * * *